US009051418B2

(12) United States Patent
Narayanan et al.

(10) Patent No.: US 9,051,418 B2
(45) Date of Patent: Jun. 9, 2015

(54) GLUCOSE-PEG CONJUGATES FOR REDUCING GLUCOSE TRANSPORT INTO A CELL

(71) Applicant: Agency for Science, Technology and Research, Singapore (SG)

(72) Inventors: Karthikeyan Narayanan, Singapore (SG); Andrew Chwee Aun Wan, Singapore (SG); Jackie Y. Ying, Singapore (SG); Nandanan Erathodiyil, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/149,493

(22) Filed: Jan. 7, 2014

(65) Prior Publication Data

US 2014/0193849 A1    Jul. 10, 2014

Related U.S. Application Data

(62) Division of application No. 13/139,170, filed as application No. PCT/SG2009/000477 on Dec. 11, 2009, now abandoned.

(60) Provisional application No. 61/193,640, filed on Dec. 11, 2008.

(51) Int. Cl.

| *A61K 31/765* | (2006.01) |
|---|---|
| *C08G 65/00* | (2006.01) |
| *A61K 31/08* | (2006.01) |
| *A61K 31/16* | (2006.01) |
| *A61K 31/69* | (2006.01) |
| *C07C 235/08* | (2006.01) |
| *C07H 15/08* | (2006.01) |
| *G01N 33/50* | (2006.01) |

(52) U.S. Cl.
CPC ............... *C08G 65/00* (2013.01); *A61K 31/08* (2013.01); *A61K 31/16* (2013.01); *A61K 31/69* (2013.01); *C07C 235/08* (2013.01); *C07H 15/08* (2013.01); *G01N 33/5091* (2013.01)

(58) Field of Classification Search
None
See application file for complete search history.

(56) References Cited

U.S. PATENT DOCUMENTS

| 2006/0014666 A1 | 1/2006 | Ji et al. |
| 2007/0287195 A1 | 12/2007 | Suda |
| 2011/0243851 A1 | 10/2011 | Narayanan et al. |

FOREIGN PATENT DOCUMENTS

| AU | 2002216097 B2 | 7/2002 |
| EP | 0080855 B1 | 1/1986 |
| PL | 191555 B1 | 6/2006 |
| PL | 191556 B1 | 6/2006 |
| WO | WO-99/11692 A1 | 3/1999 |
| WO | WO-01/77122 A1 | 10/2001 |
| WO | WO-02/50027 A1 | 6/2002 |
| WO | 2006/081510 A2 | 8/2006 |
| WO | WO-2010/068183 A1 | 6/2010 |

OTHER PUBLICATIONS

[No Author Listed], CAS RN 493020-89-6 dated Feb. 21, 2003.
[No Author Listed], CAS RN 938169-44-9 dated Jun. 21, 2007.
[No Author Listed], CAS RN 938175-58-7 dated Jun. 21, 2007.
[No Author Listed], CAS RN 938175-59-8 dated Jun. 21, 2007.
Chen et al., Carbohydrate Rod Conjugates: Ternary Rod-Coil Molecules Forming Complex Liquid Crystal Structures. JACS. vol. 127, No. 47, 2005, pp. 16578-16591. Epub Nov. 2, 2005.
Evans, A. et al., Glut-1 as a therapeutic target: increased chemoresistance and HIF-1-independent link with cell turnover is revealed though COMPARE analysis and metabolomic studies. Cancer Chemother Pharmacol. vol. 61, May 23, 2007, pp. 377-393.
International Preliminary Report on Patentability dated Nov. 15, 2010 in connection with PCT/SG2009/000477.
International Search Report and Written Opinion dated Mar. 8, 2010 in connection with PCT/SG2009/000477.
Johnsson et al., Sugar-based gemini surfactant with a vesicle-to-micelle transition at acidic pH and a reversible vesicle flocculation near neutral pH. J Am Chem Soc. Jan. 22, 2003;125(3):757-60.
Vodovozova, E. L. et al., Detection of Tumour Cell Lectins With the Help of Photoaffine Labeling. Biologicheskie Membrany. vol. 22, No. 4, 2005, pp. 308-321. English abstract included.
Wagenaar, A. et al., Synthesis of non-ionic reduced-sugar based bola amphiphiles and gemini surfactants with an alpha,omega-diamino-(oxa)alkyl spacer. Tetrahedron. vol. 63, 2007, pp. 10622-10629.
Flier, J.S. et al., "Elevated levels of glucose transport and transporter messenger RNA are induced by ras or src oncogenes", Science, 20 Mar. 1987, pp. 1492-1495, vol. 235, No. 4795.
Caplus Accession No. 2007:663804.
Haber, R.S. et al., "GLUT1 glucose transporter expression in benign and malignant thyroid nodules", Thyroid, Jun. 1997, pp. 363-367; vol. 7, Issue 3.
Yamamoto, T. et al., "Over-expression of facilitative glucose transporter genes in human cancer", Biochemical and Biophysical Research Communications, Jul. 16, 1990, pp. 223-230, vol. 170, Issue 1.
Kurata, T. et al., "Differential Expression of Facilitative Glucose Transporter (GLUT) Genes in Primary Lung Cancers and Their Liver Metastases", Japanese Journal of Cancer Research, Nov. 1999, pp. 1238-1243, vol. 90, Issue 11.
Nishioka, T. et al., "Distribution of the glucose transporters in human brain tumors", Cancer Research, 15 Jul. 1992, pp. 3972-3979, vol. 52, Issue 14.
Brown, R.S. And Wahl, R.L., "Overexpression of Glut-1 glucose transporter in human breast cancer. An immunohistochemical study", Cancer, Nov. 15, 1993, pp. 2979-2985, vol. 72, Issue 10.

(Continued)

*Primary Examiner* — James Rogers
(74) *Attorney, Agent, or Firm* — Wolf, Greenfield & Sacks, P.C.

(57) ABSTRACT

There is provided a glucose-PEG conjugate comprising a PEG moiety conjugated to a linear glucose moiety at the C1 position of the glucose moiety. The glucose-PEG conjugate may be used to reduce glucose transport into a cell and may be used to treat a proliferative disorder.

10 Claims, 9 Drawing Sheets

(56) References Cited

OTHER PUBLICATIONS

Nagase, Y. et al., "Immunohistochemical Localization of Glucose Transporters in Human Renal Cell Carcinoma", The Journal of Urology, Mar. 1995, pp. 798-801, vol. 153, Issue 3.

Baer, S.C. et al., "Expression of the human erythrocyte glucose transporter Glut1 in cutaneous neoplasia", Journal of the American Academy of Dermatology, Oct. 1997, pp. 575-577, vol. 37, Issue 4.

Ogawa, J. et al., "Glucose-transporter-type-I-gene amplification correlates with sialyl-Lewis-X synthesis and proliferation in lung cancer", International Journal of Cancer, Apr. 22, 1997, pp. 189-192, vol. 74, Issue 2.

Haber, R.S. et al., "GLUT1 glucose transporter expression in colorectal carcinoma: a marker for poor prognosis", Cancer, Jul. 1, 1998, pp. 34-40, vol. 83, Issue 1.

Wang, B.Y. et al., "Immunohistochemical staining of GLUT1 in benign, hyperplastic, and malignant endometrial epithelia", Cancer, Jun. 15, 2000, pp. 2774-2781, vol. 88, Issue 12.

Cantuaria, G. et al., "Glut-1 expression in ovarian carcinoma: Association with survival and response to chemotherapy", Cancer, Sep. 1, 2001, pp. 1144-1150, vol. 92, Issue 5.

Rudlowski, C. et al., "GLUT1 messenger RNA and protein induction relates to the malignant transformation of cervical cancer", American Journal of Clinical Pathology, Nov. 2003, pp. 691-698, vol. 120, Issue 5.

Extended European Search Report issued in corresponding EP application No. 09832210.0 dated Apr. 19, 2013.

Beckner, M.E. et al., "Glycolysis as primary energy source in tumor cell chemotaxis", Journal of the National Cancer Institute, Dec. 5, 1990, pp. 1836-1840, vol. 82, Issue 23.

Newsholme, E.A. and Board, M., "Application of metabolic-control logic to fuel utilization and its significance in tumor cells", Advances in Enzyme Regulation, 1991, pp. 225-246, vol. 31.

Warburg, O., "On the origin of cancer cells", Science, Feb. 24, 1956, pp. 309-314, vol. 123, No. 3191.

Shim, H. et al., "c-Myc transactivation of LDH-A: Implications for tumor metabolism and growth", Proceedings of the National Academy of Sciences of the United States of America, Jun. 24, 1997, pp. 6658-6663, vol. 94, Issue 13.

Board, M. et al., "Maximum activities of key enzymes of glycolysis, glutaminolysis, pentose phosphate pathway and tricarboxylic acid cycle in normal, neoplastic and suppressed cells", Biochemical Journal, Jan. 15, 1990, pp. 503-509, vol. 265, Issue 2.

Mazurek, S. et al., "Pyruvate kinase type M2: a crossroad in the tumor metabolome", British Journal of Nutrition, Jan. 1, 2002, pp. S23-S29, vol. 87, Issue S1.

Hennipman, a. et al., "Glycolytic enzyme activities in breast cancer metastases", Tumor Biology, 1988, pp. 241-248, vol. 9, Issue 5.

Zamora-León, S.P. et al., Expression of the fructose transporter GLUT5 in human breast cancer', Proceedings of the National Academy of Sciences of the United States of America, Mar. 5, 1996, pp. 1847-1852, vol. 93, Issue 5.

Connors, T.A. et al., "Some studies of the active intermediates formed in the microsomal metabolism of cyclophosphamide and iphosphamide", Biochemical Pharmacology, Jan. 1, 1974, pp. 115-129, vol. 23, Issue 1.

Reske, S.N. et al., "Overexpression of glucose transporter 1 and increased FDG uptake in pancreatic carcinoma", Journal of Nuclear Medicine, Sep. 1, 1997, pp. 1344-1348, vol. 38, Issue 9.

Veyhl, M. et al., "Transport of the new chemotherapeutic agent b-D-glucosylisophosphoramide mustard (D-19575) into tumor cells is mediated by the Na+-D-glucose cotransporter SAAT1", Proceedings of the National Academy of Sciences of the United States of America, Mar. 17, 1998, pp. 2914-2919, vol. 95, Issue 6.

Pohl, J. et al., "D-19575—a sugar-linked isophosphoramide mustard derivative exploiting transmembrane glucose transport", Cancer Chemotherapy and Pharmacology, Jan. 1995, pp. 364-370, vol. 35, Issue 5.

Ball, H.A. et al., "Influence of glucose anti-metabolites on the Walker tumor", Cancer Research, Apr. 1957, pp. 235-239, vol. 17, Issue 3.

Laszlo, J. et al., "Effects of glucose analogues (2-deoxy-D-glucose, 2-deoxy-D-galactose) on experimental tumors", Journal of the National Cancer Institute, Feb. 1960, pp. 267-281, vol. 24.

Kern, K. And Norton, J., "Inhibition of established rat fibrosarcoma growth by the glucose antagonist 2-deoxy-D glucose", Surgery, Aug. 1987, pp. 380-385, vol. 102, Issue 2.

Nelson, C. et al., "The interaction among glucose transport, hexokinase, and glucose-6-phosphatase with respect to 3H-2-deoxyglucose in murine tumor models", Nuclear Medicine and Biology, May 1996, pp. 533-541, vol. 23, Issue 4.

Aft, R.L. et al., "Evaluation of 2-deoxy-D-glucose as a chemotherapeutic agent: Mechanism of cell death", British Journal of Cancer, Oct. 2002, pp. 805-812, vol. 87, Issue 7.

Ko, Y.H. et al., "Glucose catabolism in the rabbit VX2 tumor model for liver cancer: Characterization and targeting hexokinase", Cancer Letters, Nov. 8, 2001, pp. 83-91, vol. 173, Issue 1.

Noguchi, Y. et al., "Suppression of facilitative glucose transporter 1 mRNA can suppress tumor growth", Cancer Letters, Jun. 30, 2000, pp. 175-182, vol. 154, Issue 2.

Rastogi, S. et al., "Glut-1 antibodies induce growth arrest and apoptosis in human cancer cell lines", Cancer Letters, Nov. 18, 2007, pp. 244-251, vol. 257, Issue 2.

Lee, G.Y. et al., "Glucosylated heparin derivatives as non-toxic anti-cancer drugs", Journal of Controlled Release, Oct. 18, 2007, pp. 46-55, vol. 123, Issue 1.

Airley, R.E. And Mobasheri, a., "Hypoxic regulation of glucose transport, anaerobic metabolism and angiogenesis in cancer: Novel pathways and targets for anticancer therapeutics", Chemotherapy, Jul. 2007, pp. 233-256, vol. 53, Issue 4.

Maher, J.C. et al., "Hypoxia-inducible factor-1 confers resistance to the glycolytic inhibitor 2-deoxy-D-glucose", Molecular Cancer Therapeutics, Feb. 2007, pp. 732-741, vol. 6, Issue 2.

Cao, X. et al., "Glucose uptake inhibitor sensitizes cancer cells to daunorubicin and overcomes drug resistance in hypoxia", Cancer Chemotherapy and Pharmacology, Mar. 2007, pp. 495-505, vol. 59, No. 4.

Grover-McKay, M. et al., "Role for glucose transporter 1 protein in human breast cancer", Pathology & Oncology Research, Jun. 1998, pp. 115-120, vol. 4, No. 2.

Kawamura, T. et al., "Expression of glucose transporter-1 in human gastric carcinoma: Association with tumor aggressiveness, metastasis, and patient survival", Cancer, Aug. 1, 2001, pp. 634-641, vol. 92, Issue 3.

Rivenzon-Segal, D. et al., "Glucose transporters and transport kinetics in retinoic acid-differentiated T47D human breast cancer cells", American Journal of Physiology — Endocrinology and Metabolism, Sep. 1, 2000, pp. E508-E519, vol. 279, Issue 3.

Ravazoula et al., Immunohistochemical expression of glucose transporter Glut1 and cyclin D1 in breast carcinomas with negative lymph nodes. Eur J Gynaecol Oncol. 2003;24(6):544-6.

Younes et al., GLUT1 expression in human breast carcinoma: correlation with known prognostic markers. Anticancer Res. Nov.-Dec. 1995;15(6B):2895-8.

| Cell line tested | Compound | Cell viability ± SD |
|---|---|---|
| Gastric cancer (AGS) | BrP | 95.8 ± 11.4 |
| | GBrP | 12.5 ± 7.8 |
| Lung cancer (H1299) | BrP | 96.3 ± 7.3 |
| | GBrP | 28.1 ± 6.9 |
| Liver cancer (HepG2) | BrP | 90.3 ± 14.6 |
| | GBrP | 17.1 ± 2.5 |
| Prostate cancer (DU145) | BrP | 98.8 ± 8.1 |
| | GBrP | 18.9 ± 4.7 |
| Colon cancer (Caco2) | BrP | 94.6 ± 7.8 |
| | GBrP | 9.8 ± 4.2 |
| Breast cancer (MCF-7) | BrP | 92.8 ± 4.5 |
| | GBrP | 9.3 ± 1.3 |
| Normal breast cells (MCF-10A) | BrP | 93.1 ± 4.3 |
| | GBrP | 70.7 ± 7.3 |

TABLE 1

FIG. 13

GLUCOSE-PEG CONJUGATES FOR
REDUCING GLUCOSE TRANSPORT INTO A
CELL

CROSS-REFERENCE TO RELATED
APPLICATIONS

This application is a divisional application of U.S. patent application Ser. No. 13/139,170, filed Jun. 10, 2011, which is a U.S. National Stage application based on International Application No. PCT/SG2009/000477, filed Dec. 11, 2009, which claims benefit of, and priority from, U.S. provisional patent application No. 61/193,640, filed on Dec. 11, 2008, the contents of which are incorporated herein by reference in their entirety.

FIELD OF THE INVENTION

The present invention relates to glucose-polyethylene glycol conjugates and the use of such conjugates to reduce glucose transport into a cell.

BACKGROUND OF THE INVENTION

One of the key characteristics of cancer cells is the increased rate of proliferation. Often the rate of proliferation exceeds de novo vascular formation. As a result, tumor cells may out-grow the available blood supply, and shortage of blood leads to hypoxia (low oxygen level). To overcome hypoxia, tumor cells tend to rely on glycolysis for ATP production (17). High glycolysis rate is characteristic of solid tumors, and is associated with an over-expression of glucose transporters (GLUTs) and glycolytic enzymes.

Thus, a high rate of glucose uptake and increased glucose metabolism are involved in maintaining proliferation of tumor cells (18). This phenomenon is commonly known as Warburg effect (19). It was observed that the initial high level of anaerobic glycolysis resulted in the accumulation of lactate (20). The enzyme (lactate dehydrogenase) responsible for the conversion of pyruvate to lactate was also observed to be elevated in the cancer cells (20). However, lactate dehydrogenase also helps in the survival of the cells under hypoxic conditions by anaerobic glycolysis (20). Increased glycolytic enzyme activities have been reported in cancerous cells (21, 22), and have been observed with the progression of cancer from primary breast tumor to the metastatic stage (23, 24).

Transport of glucose across the membrane of cells is facilitated by proteins called glucose transporters (GLUTs). 13 GLUTs have been identified to date, and have been categorized into three classes. Class I includes GLUT1 to GLUT4, class II includes GLUT5, GLUT7, GLUT9 and GLUT11, and class III includes GLUT6, GLUT5, GLUT10, GLUT12 and GLUT13. The different transporters have different kinetics and affinities towards glucose and other hexoses. The expression level of the different GLUTS in various tissues varies depending on the metabolic consumption of glucose by the particular tissue type. GLUT1 is a ubiquitously expressed GLUT and GLUT1 and GLUT3 expression levels have been found to be much higher in cancerous cells than in normal cells (1). This overexpression has been observed in a wide variety of different cancer cell types (2-14). Extensive studies with breast cancer patients indicated increased GLUT1 activity among the patients (15, 16).

Metabolic targeted cancer therapy is a relatively new field in cancer therapeutic research and is designed to take advantage of the inherent hyper-metabolic characteristics of cancer cells.

Certain previous studies focused on developing therapeutic drugs based on the metabolism of cancer cells. Glufosfamide is a small molecule generated by the conjugation of ifosfamide and glucose. This compound enters the cancer cells through the GLUT proteins. It breaks down in the cell, leading to the release of the toxin (ifosfamide) inside the cell (25-28).

Other groups have used different glucose analogs in an attempt to reduce the glucose metabolism in cancer cells (29, 30). Of the various compounds, 2-deoxyglucose (2-DG) has been shown to be a promising analog. 2-DG is an orally administered glucose analog that inhibits the glycolysis pathway of ATP production in cancer cells. 2-DG accumulates in the cancer cells because the phosphorylated 2-DG cannot be processed by glycolytic enzymes (31, 32). 2-DG can elicit 50% apoptotic cells at a concentration of 4 mM in the SkBr3 (human breast cancer) cell line (33). In vivo animal studies with 2-DG have shown that the growth of the tumor was inhibited with supplemental 2-DG (31, 34).

Noguchi et al. have used anti-sense against GLUT-1 to suppress tumor growth in MKN45 (gastric cancer) cell line. Comparison of tumor development in nude mice demonstrated that the cells expressing anti-sense GLUT-1 develop tumor much more slowly than the wild-type cells (35).

In a more recent study, monoclonal antibody against GLUT-1 was shown to induce growth arrest and apoptosis in breast cancer and lung cancer cell lines. 50% and 75% reductions in cell growth were found in lung cancer and breast cancer cell lines, respectively (36).

SUMMARY OF THE INVENTION

The present invention relates to novel glucose-polyethylene glycol (glucose-PEG) conjugates and their use to reduce glucose transport into a cell. Thus, the glucose-PEG conjugates may be useful to reduce cellular proliferation, particularly in respective of proliferative disorders, such as cancer. The glucose-PEG conjugates of the present invention may also be labelled with a detectable label, and thus may be useful for imaging of hyper-proliferative cells such as cancer cells.

The present invention takes advantage of the overexpression of GLUTs in hyper-proliferative cells in order to control cellular proliferation, potentially leading to the death of the hyper-proliferative cells. The glucose-PEG conjugate may be used to target and induce apoptosis in hyper-proliferating cells, such as cancer cells, as a result of reduced glucose transport into the cells. Cancer cells often thrive on glycolytic enzymes that break down glucose into ATP in an anaerobic process. Glucose uptake by the GLUTs has been shown to be high in many cancerous cells and tissues. The glucose-PEG conjugates of the present invention are able to bind to the GLUTs, thus taking advantage of the GLUT overexpression in hyper-proliferative cells such as cancer cells. The glucose-PEG conjugates are not transported into the cells and thus binding of the glucose-PEG conjugates to a GLUT reduces the availability of GLUTs for transporting glucose into the cell, potentially triggering apoptosis.

Thus, the glucose-PEG conjugates of the present invention may be useful to control proliferation of hyper-proliferative cells such as cancer cells, including tumor cells within a tumor core where blood vascularization may be limited. Direct injection into the tumor core may reduce proliferation of the tumor while having minimal effect on surrounding healthy tissue.

In one aspect, the invention provides a glucose-PEG conjugate comprising a PEG moiety conjugated to a linear glucose moiety at the C1 position of the glucose moiety.

Conjugation of the PEG moiety to the C1 position of the glucose moiety may occur via an amine linkage.

The PEG moiety may comprise a linear, branched, dendritic, hyperbranched, star or comb PEG, and may be terminated at one or both ends with an end group.

The glucose-PEG conjugate may further comprise a linker moiety connecting the PEG moiety to the glucose moiety.

The glucose-PEG conjugate may also further comprise a detectable label. The detectable label may be a PET label, an SPECT label, an MRI label, a quantum dot label, a coloured label, a fluorescent label, a radiolabel or a label that may be detected by an antibody or antibody fragment.

In another aspect, the invention provides a method of reducing glucose transport into a cell comprising contacting the cell with a glucose-PEG conjugate as described herein. The cell may be a hyper-proliferative cell.

In another aspect, the invention provides a method of imaging a hyper-proliferative cell comprising contacting a hyper-proliferative cell with a glucose-PEG conjugate as described herein comprising a detectable label; and detecting the detectable label.

The detecting may involve fluorescence microscopy, positron emission tomography imaging, single photon emission computed tomography imaging or magnetic resonance imaging.

In the above described methods, the cell may be an in vitro cell. Alternatively, the cell may be an in vivo cell, including a cell that is associated with a proliferative disorder. Thus, contacting may include administering an effective amount of the glucose-PEG conjugate at the site of a hyper-proliferating cell in a subject.

The above described methods may further comprise contacting the cell with a chemotherapeutic agent.

In another aspect, the invention provides a pharmaceutical composition comprising a glucose-PEG conjugate as described herein.

In another aspect, the invention provides use of a glucose-PEG conjugate as described herein, including use in the preparation of a medicament, for reducing glucose transport into a cell.

In another aspect, the invention provides use of a glucose-PEG conjugate as described herein, including use in the preparation of a medicament, for treating a proliferative disorder in a subject.

In another aspect, the invention provides use of a glucose-PEG conjugate as described herein comprising a detectable label, including use in the preparation of a composition, for imaging a hyper-proliferative cell.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The figures illustrate, by way of example only, embodiments of the present invention, are as described below.

FIG. 13: Table 1 shows the effects of GBrP and branched PEG (BrP) on different cancer cell lines and on normal breast epithelial cells (MCF-10A). Cells were treated as described in FIG. 3, with 200 µM of either BrP or GBrP. MTT assay was carried out to monitor the viability of the cells. Values obtained for the cells without any treatments were kept as 100%.

DETAILED DESCRIPTION

Figure 1:
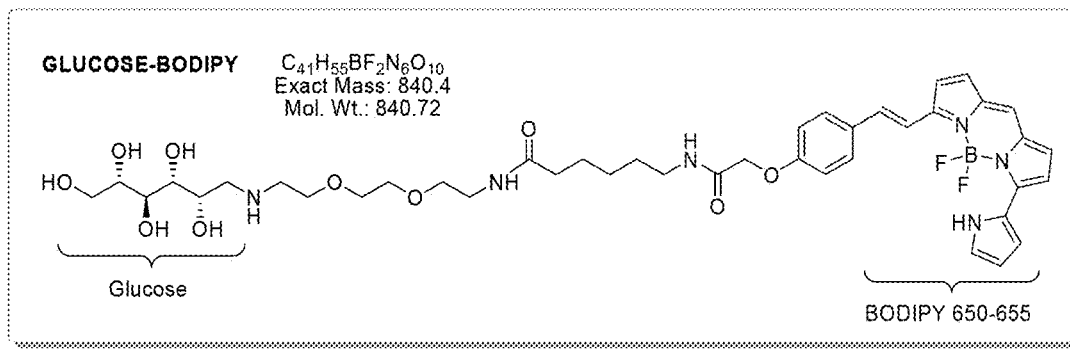
FIG. 1: Structure of an exemplary glucose-PEG-BODIPY. The PEG moiety is depicted as only two repeating ethyloxo units. However, the PEG moiety may be larger.

Thus, there is provided a glucose-PEG conjugate, having the PEG moiety conjugated to a linear glucose moiety at the C1 position of the glucose.

The glucose moiety of the glucose-PEG conjugate is a linear glucose, meaning that the glucose is in an open form and has not cyclised. Cyclic glucose is the form of glucose typically found in biological systems, in which the C1 to C5 carbons, together with an oxygen atom, form a six-membered ring. In contrast, in the glucose-PEG conjugate, the glucose is linear, leaving the C1 position available for conjugation to the PEG moiety. The linear glucose is still able to bind to the GLUTs, but the linear form of glucose is not typically found in biological systems, and does not tend to enter glycolytic metabolic pathways.

The PEG moiety may be any PEG moiety. As will be appreciated, polyethylene glycol or poly(ethylene glycol) refers to a polymer made up of monomers of ethylene glycol condensed to form the polymer.

The PEG used may be monodispersed, meaning the PEG preparation or solution used to form the conjugate has chains of uniform length, or may be polydispersed, meaning the PEG preparation or solution used has chains of varying length. The PEG moiety of the glucose-PEG conjugate may be of any length, for example from 2 to 500 repeating units, or having an average molecular weight of from about 300 g/mol to about 10,000,000 g/mol. In various embodiments, the PEG may be (all average molecular weight) PEG 200, PEG 300, PEG 400, PEG 600, PEG 800, PEG 1000, PEG 1500, PEG 2000, or PEG 3350.

The PEG moiety may be a linear PEG. Alternatively, the PEG may be a branched PEG. Branched PEG includes any PEG having one or more branches of PEG groups extending from a PEG backbone, and includes specific arrangements or degrees of branching, such as a hyperbranched PEG, a dendritic PEG, a star PEG, or a comb PEG. In a particular embodiment, the PEG is a branched PEG.

The PEG used to form the conjugate may be terminated at one or both ends with an end group, for example an amino group, a hydroxyl group, a methyl ether group, a caprolactone group, a carbohydrate moiety or one or more amino acids.

The PEG moiety is conjugated to the linear glucose moiety at the C1 position of the glucose molecule. The C1 position in free linear glucose is part of an aldehyde functional group, that is, in free linear glucose the C1 carbon atom is bonded to an oxy functional group and a hydrogen atom, as well as to the C2 carbon atom. In the conjugate, the oxy portion of the aldehyde group may be removed by the conjugation of the PEG moiety, or may be involved in the conjugation reaction and thus may be converted to another functional group, for example the oxy group may become an oxo group, forming an ether linkage to the PEG moiety. Thus, the PEG moiety (or an end group on the PEG moiety) may be bonded directly to the C1 carbon or may be bonded to the oxygen of the aldehyde group. In particular embodiments, the PEG used to form the conjugate has a free primary amino group at least at the terminus that is to be conjugated to the C1 position of the linear glucose, and following conjugation, the oxy group is replaced by a secondary amino group connecting the linear glucose moiety to the PEG moiety via an amine linkage.

The PEG moiety, including an end group, may be directly attached to the linear glucose moiety at the C1 position, or may be attached via a linker moiety. For example, a linker that is connected to the C1 position of glucose (or via reaction with the aldehyde functionality at the C1 position), may also be attached to the PEG moiety, including an end group on the PEG moiety, thus linking together the glucose moiety and the PEG moiety via an attachment at the C1 carbon, as described above.

Optionally, the glucose-PEG conjugate may include a detectable label. The label may be attached anywhere on the glucose-PEG conjugate, including attached to the PEG moiety, and may be attached for example at the free end of the PEG moiety or (end group) not conjugated to the glucose moiety.

The detectable label may be any label that is detectable using known detection methods, including imaging methods. For example, the detectable label may be a PET label, an SPECT label, an MRI label, a quantum dot label, a coloured label, a fluorescent label, a radiolabel or a label that may be detected by an antibody or antibody fragment. Such labels are known and are readily available. For example, fluorescent labels include BODIPY, FITC, Rhodamine, TRITC, Texas Red, cyanine dyes (e.g. Cy3 or Cy5) or Alexa fluors. Radiolabels include moieties or groups having at least one radioactive isotope, and include moieties or groups having a positron emitting radioactive isotope or a gamma emitting radioactive isotope.

In particular, radiolabels such as PET labels useful for PET scanning may include an unstable positron-emitting isotope. Such isotopes may be synthesized in a cyclotron by bombarding nitrogen, carbon, oxygen, or fluorine with protons. Examples of the isotopes used for PET labels include $^{15}$O (half-life: 2 min), $^{18}$F (half-life: 110 min), and $^{11}$C (half-life: 20 min). Positron or photon emitting atoms such as $^{18}$F, $^{11}$C, $^{125}$I, $^{123}$I, $^{16}$N, $^{15}$O, $^{3}$H, $^{133}$Xe, $^{111}$In, $^{68}$Ga and other isotopes of metals such as technetium, or copper may be used in PET labels or SPECT labels. MRI labels include T1 (Gd) and T2 ($Fe_3O_4$) contrast agents.

Figure 2:
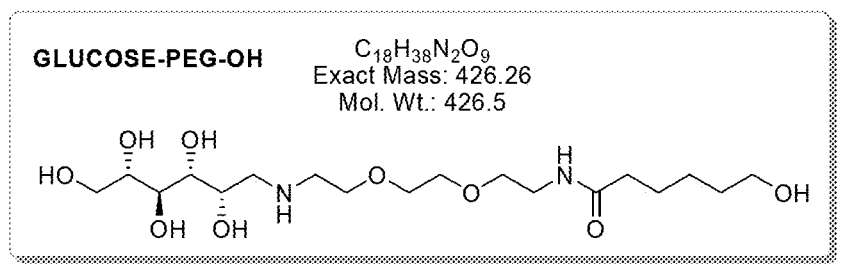
FIG. 2: Structure of an exemplary glucose-PEG-OH, synthesized by conjugating glucose with an amino-terminated PEG and then reaction with caprolactone. As with FIG. 1, the PEG moiety may be larger than depicted.
Figure 3:
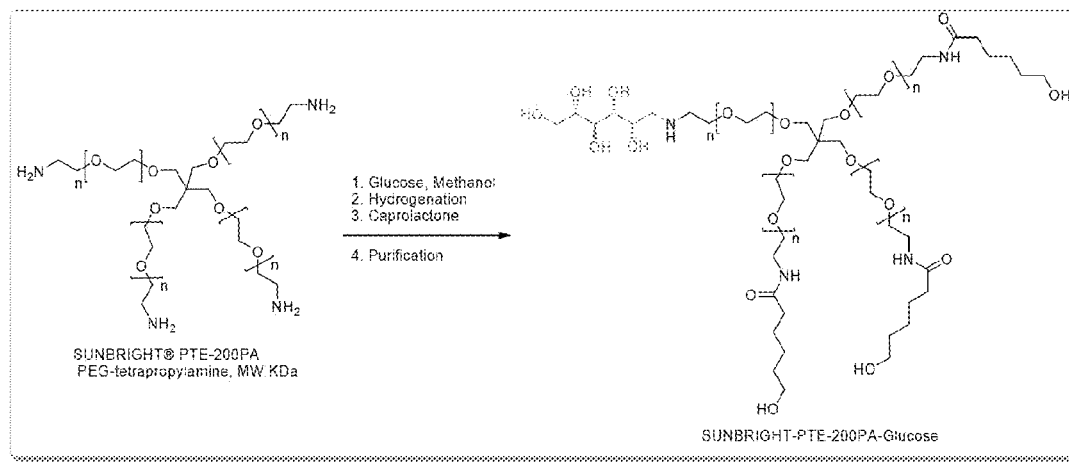
FIG. 3: Structure of an exemplary glucose-branched PEG synthesized by conjugating glucose with an amino-terminated branched PEG and then reaction with caprolactone. Each n is independently greater than or equal to 1.

In particular embodiments, the glucose-PEG conjugate comprises the conjugate depicted in FIG. 1, FIG. 2 or FIG. 3. In particular embodiments, the glucose-PEG conjugate is the conjugate depicted in FIG. 1, FIG. 2 or FIG. 3. For FIG. 3, each n is independently 1 or greater, or from 1 to 500. In other embodiments, the glucose-PEG conjugate has the arrangement as depicted in FIG. 1 or FIG. 2, but having the PEG moiety longer than depicted in the relevant Figure, up to 500 repeating ethylene glycol units.

Figure 4:
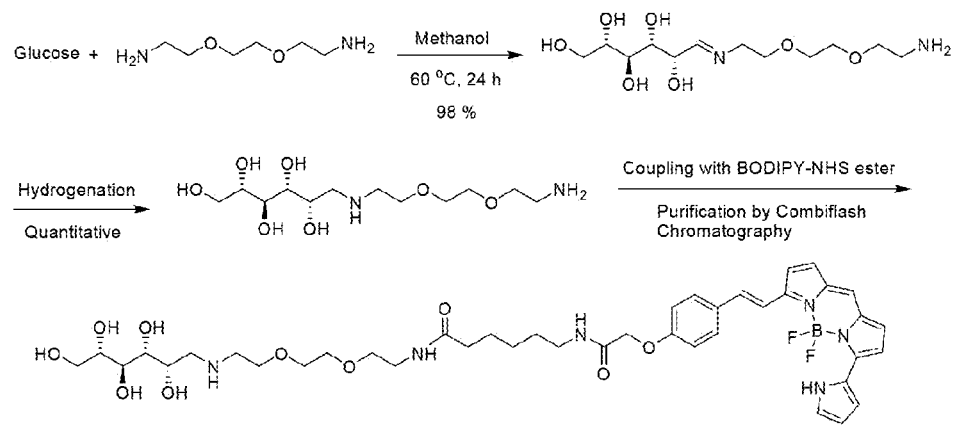
FIG. 4: Synthetic scheme for synthesis of glucose-PEG-BODIPY.

The glucose-PEG conjugates may be synthesized using standard known organic synthesis methods. Linear glucose and various PEGs are readily commercially available. Conjugation may be readily performed using known reactions to reaction an appropriate functional group on the terminus of the PEG molecule or on a linker molecule with the free aldehyde located at the C1 position of the linear glucose molecule. Similarly, standard chemical coupling reactions may be used to attach any detectable label, including attachment to the PEG moiety, either before or after conjugation to the glucose moiety.

Where the PEG used is terminated with an end group having a free amino group or where a linker molecule with a free amino group is used, conjugation of the amino group with the C1 carbon atom may be performed in accordance with Example 1 set out below, and the synthetic scheme described in FIG. 4.

As stated above, it appears that the glucose-PEG conjugate binds to the GLUTs but is not transported into the cell. Without being limited to any particular theory, the glucose-PEG conjugate appears to bind to the GLUTs, blocking binding and transport of glucose, thus reducing the cell's internal glucose supply available for glycolysis, and thus reducing the proliferation rate of the cell. The cell surface of the normal cells contains glucose transporters along with transporters for other saccharides such as fructose and galactose. However, in hyper-proliferating cells such as cancer cells, glucose transporters are the primary transporters and the cancer cells depend on the glucose intake for their ATP generation and oxygen production under anaerobic conditions. Blocking the glucose receptors in hyper-proliferating cancer cells may lead to cell death, as was found in studies involving siRNA and antibody based blockage of the glucose receptors leading to cell death in proliferating cancer cells.

Since the linear form of glucose used in the glucose-PEG conjugate typically does not participate in glycolytic metabolic pathways, even if the conjugate were to degrade in vivo to release the linear glucose moiety from the conjugate, no cyclic glucose (or cyclizable glucose) would be made available and thus would not result in increased glycolysis by cells. This is in contrast to other glucose analogues and conjugates, which typically use cyclic glucose or glucose which is able to cyclise due to availability of the C1 aldehyde functionality to form the cyclic form of glucose. Such cyclic glucose analogues and conjugates may contribute to the glucose supply within a cell should the analogue or conjugate be degraded to release free glucose.

Furthermore, the PEG portion of the conjugate is highly soluble, and is generally biologically inert, biodegradable, non-toxic and non-immunogenic. Thus, the glucose-PEG conjugated described herein is useful for reducing glucose uptake by a cell, including in in vivo contexts.

Thus, in another aspect, there is provided a method of reducing glucose transport into a cell comprising contacting the cell with a glucose-PEG conjugate as described herein. Contacting the cell with the conjugate thus allows the conjugate to bind to the GLUTs on the surface of the hyper-proliferative cell.

Glucose transport into a cell refers to the process of moving glucose from the exterior of a cell into the interior of the cell, including that mediated by GLUTs. Reducing glucose transport in a cell refers to lessening the amount of glucose that is taken up into the cell, including via transport by GLUTs. Reducing includes lessening as well as completely blocking glucose transport, including glucose transport by GLUTs. Reducing may lead to slowing of proliferation by the cell so that the cell still proliferates but not as quickly as in the absence of the glucose-PEG conjugate, or may lead to cessation of proliferation, or even cell death, including apoptotic cell death.

The term cell as used herein refers to and includes a single cell, a plurality of cells or a population of cells where context permits, unless otherwise specified. Similarly, reference to cells also includes reference to a single cell where context permits, unless otherwise specified.

The cell may be any cell, including an in vitro cell, a cell in culture, an in vivo cell, or an ex vivo cell explanted from a subject.

The cell may be derived from any organism that expresses GLUTs and that undergoes anaerobic glycolysis, for example an animal, including a mammal, including a human. The cell may be a primary cell or it may be a cell from an established cell line, including a cancer cell line.

The cell may be a hyper-proliferative cell. As used herein, a hyper-proliferative cell or hyper-proliferating cell is a cell in which proliferation is uncontrolled or is increased relative to a healthy cell. A healthy cell is a cell of the same cell type but that is not hyper-proliferating or in which proliferation is under normal cellular controls. The hyper-proliferative cell may be a cell associated with a proliferative disorder, including a cell within a solid tumor, and may be a cell that is being treating with a further cancer therapy.

A cell is associated with a proliferative disorder if that cell is a cell that is abnormally proliferating so as to result in the disorder in a subject in which the cell is located, or if the disorder is characterized by the proliferation of such a cell.

A proliferative disorder is a disease or disorder in which a cell of a subject is abnormally proliferating, resulting in uncontrolled growth and division of the cell, which in a healthy individual would not be proliferating or would be proliferating in a controlled manner. The proliferative disorder may be characterized by the proliferation of malignant or non-malignant cell populations, including in a solid tumor. Such disorders include cancer including breast cancer, liver cancer, gastric cancer, bladder cancer, colon cancer, prostate cancer, lung cancer, nasopharyngeal carcinoma, cervical carcinoma, skin cancer.

Where the cell is an in vitro cell, including a cell in culture and/or an explanted cell, contacting the cell with the glucose-PEG conjugate may comprise adding the conjugate to the buffer solution or growth medium in which the cell is contained.

The glucose-PEG conjugate may be added to the buffer solution or growth medium at a concentration of about 0.01 mM or greater, about 0.02 mM or greater, about 0.05 mM or greater or about 1.0 mM or greater. Alternatively, the glucose-PEG conjugate may be added to the buffer solution or growth medium at a concentration of from about 0.01 mM to about 20 mM, about 0.02 to about 10 mM, or about 0.02 to about 0.5 mM.

If desired, the glucose-PEG conjugate may comprise a detectable label as described above, in order to allow for confirmation that the conjugate is binding to the GLUTs on the exterior surface of the cell by detecting the location of the conjugate after contacting with a cell. Thus, the method in certain embodiments may comprise detecting the glucose-PEG conjugate after contacting with the cell. The detecting may include imaging of the cell, including using known fluorescent imaging techniques in vitro.

Where the cell is an in vivo cell, contacting the cell with the glucose-PEG conjugate may comprise administering an effective amount of the conjugate to a subject.

The term "effective amount" as used herein means an amount effective, at dosages and for periods of time necessary to achieve the desired result, for example, to reduce glucose transport in the cell or to treat the specific proliferative disorder.

Since reducing glucose transport into a hyper-proliferative cell may result in starvation of the cell, resulting in slowing of proliferation, cessation of proliferation, or even cell death, the method may include treatment of a proliferative disorder in a subject.

The term "treating" a proliferative disorder refers to an approach for obtaining beneficial or desired results, including clinical results. Beneficial or desired clinical results can include, but are not limited to, alleviation or amelioration of one or more symptoms or conditions, diminishment of extent of disease, stabilization of the state of disease, prevention of development of disease, prevention of spread of disease, delay or slowing of disease progression, delay or slowing of disease onset, amelioration or palliation of the disease state, and remission (whether partial or total). "Treating" can also mean prolonging survival of a patient beyond that expected in the absence of treatment. "Treating" can also mean inhibiting the progression of disease, slowing the progression of disease temporarily, although more preferably, it involves halting the progression of disease permanently.

The subject is any animal in need of treatment of a proliferative disorder, including a mammal, including a human.

The conjugate may be administered to the subject using standard techniques known in the art. The conjugate may be administered systemically, or may be administered directly at the site at which the proliferating cell that is associated with the proliferative disorder is located. Delivery to the site includes topical administration, injection or surgical implantation, including at a site of a tumor. Delivery may be performed using a drug delivery device, to allow sustained delivery of the conjugate according to a desired release profile. Drug delivery devices including transdermal systems as well as devices for implantation.

The concentration and amount of the conjugate to be administered will vary, depending on the proliferative disorder to be treated, the type of cell associated with the proliferative disorder, the type of conjugate that is administered, the mode of administration, and the age and health of the subject.

Optionally, the method also involves imaging of hyperproliferative cells in vivo. Thus, as described above, the conjugate may comprise a detectable label, including a fluorescent marker, an MRI label, a PET label, a SPECT label, a radiolabel or a quantum dot, suitable for detection using in vivo imaging techniques.

Since the conjugate can influence the growth of hyperproliferative cells, the conjugate may be used in combination with other cancer treatments, including to target drug-resistant cancer cells to make such cells more susceptible to treatment by cancer treatments such as with chemotherapeutic agents.

Thus, the reducing and/or treating may be further accomplished in combination with a chemotherapeutic agent. In combination with a chemotherapeutic agent means that the reducing and/or treating occurs in a time period during which a chemotherapeutic agent is contacted with or administered to the cell. The reducing of glucose transport and the contacting with or administration of the chemotherapeutic agent may occur simultaneously or sequentially, and the respective time period for each may be conterminous or may be overlapping provided that the benefit or effect of the chemotherapy treatment is ongoing in the cell concomitantly with the reducing. The reducing and the administration each may be achieved in one or more discrete treatments or may be performed continuously for a given time period required in order to achieve the desired result.

The cell may be further contacted with the chemotherapeutic agent in a manner similar to that described above for contacting with the conjugate, depending on the nature of the chemotherapeutic agent. The cell may be contacted with the chemotherapeutic agent prior to, following, or simultaneously with the conjugate.

The chemotherapeutic agent may be a compound that is typically administered to a cell and which has a cytotoxic or cytostatic effect. The chemotherapeutic agent may be an agent that induces apoptosis, such as p53-dependent apoptosis, or that induces cell cycle arrest, including p53-dependent cell cycle arrest, in a cell that is abnormally proliferating, even in the absence of the conjugate. The chemotherapeutic agent may also be an agent that activates p53 or p21 in an abnormally proliferating cell but that does not induce apoptosis in the cell, due to a property of the abnormally proliferating cell, for example an alteration or mutation in p53 or in the p53 pathways. Treatment of the cell with the chemotherapeutic agent in combination with the conjugate induces cell death, or increases sensitivity to cell death, at a level greater than that which is observed in the absence of the conjugate.

The chemotherapeutic agent may be a DNA damaging agent or a genotoxic agent that can activate p53-dependent apoptosis or p53-dependent cell cycle arrest in a proliferating cell. The chemotherapeutic agent may be, without limitation, a small molecule, a peptide or a protein, an anthracycline, an alkylating agent, an alkyl sulfonate, an aziridine, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. The chemotherapeutic agent may be chosen as a chemotherapeutic agent that is known to be effective against the particular cellular proliferative disorder and cell type. In certain embodiments the chemotherapeutic agent is cisplatin, paclitaxel, Adriamycin (ADR), 5-fluorouracil (5-FU), etoposide, or camptothecin or a derivative or analog thereof.

Also contemplated are various uses of the glucose-PEG conjugate, including use of the conjugate for reducing glucose transport into a cell, or for treating a proliferative disorder in a subject. The use may include use in the manufacture of a medicament or pharmaceutical composition.

Thus, to aid in administration to a subject, the glucose-PEG conjugate may be formulated as an ingredient in a pharmaceutical composition. Therefore, in a further embodiment, there is provided a pharmaceutical composition comprising a glucose-PEG conjugate, and may further include a pharmaceutically acceptable diluent. The invention in one aspect therefore also includes such pharmaceutical compositions for use in reducing glucose transport in a cell and/or for use in treating a proliferative disorder.

The pharmaceutical compositions may routinely contain pharmaceutically acceptable concentrations of salt, buffering agents, preservatives and various compatible carriers. For all forms of delivery, the glucose-PEG conjugate may be formulated in a physiological salt solution.

The pharmaceutical composition can be prepared by known methods for the preparation of pharmaceutically acceptable compositions suitable for administration to patients, such that an appropriate quantity of the glucose-PEG conjugate, and any additional active substance or substances, is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of the glucose-PEG conjugate, in association with one or more pharmaceutically acceptable vehicles or diluents, and contained in buffer solutions with a suitable pH and iso-osmotic with physiological fluids. A person skilled in the art would know how to prepare suitable formulations.

The proportion and identity of the pharmaceutically acceptable diluent is determined by chosen route of administration, compatibility with live cells, and standard pharmaceutical practice. Generally, the pharmaceutical composition will be formulated with components that will not significantly impair the properties of the glucose-PEG conjugate to reduce glucose transport into a cell.

The pharmaceutical compositions may additionally contain other therapeutic agents useful for treating the particular proliferative disorder, for example a cytotoxic agent, for example a chemotherapeutic agent.

The pharmaceutical composition may be administered to a subject in a variety of forms depending on the selected route of administration, as will be understood by those skilled in the art.

In different embodiments, the composition is administered topically, surgically or by injection (subcutaneously, intravenously, intramuscularly, etc.) directly at the desired site where the cells that are proliferating in an uncontrolled manner are located in the patient, including at or within a tumor.

The dose of the pharmaceutical composition that is to be used depends on the particular condition being treated, the severity of the condition, the individual patient parameters including age, physical condition, size and weight, the duration of the treatment, the nature of concurrent therapy (if any), the specific route of administration and other similar factors that are within the knowledge and expertise of the health practitioner. These factors are known to those of skill in the art and can be addressed with minimal routine experimentation.

In another aspect, there is provided a method of imaging a hyper-proliferative cell, including both in vitro and in vivo.

Terms used in describing this method are those as defined above, unless otherwise indicated.

The method of imaging includes contacting a cell with a glucose-PEG conjugate as described herein, the conjugate comprising a detectable label; and detecting the detectable label in order to image the hyper-proliferative cell.

As indicated above, the detectable label is any label that is detectable using standard detection methods, including imaging methods. In vitro imaging methods include fluorescence microscopy techniques. Imaging methods for in vivo imaging include magnetic resonance imaging (MRI) including functional magnetic resonance imaging (fMRI) techniques, positron emission tomography (PET) imaging techniques, and single photon emission computed tomography (SPECT) imaging techniques.

The glucose-PEG conjugate is contacted with the hyper-proliferative cell in a manner as described above to allow the conjugate to bind to the GLUTs on the surface of the hyper-proliferative cell. For example, for an in vitro cell, the glucose-PEG conjugate may be added to a buffer or culture medium containing the cell. For example, for an in vivo cell, the glucose-PEG conjugate may be administered to a subject in which a hyper-proliferative cell is desired to be imaged, as described above, including by topical administration, injection or surgical implantation, including at a site of a tumor. As described above, inclusion of the conjugate in a composition may aid in administration of the conjugate to a subject.

Once contacted with the cell, the hyper-proliferative cell may be incubated with the glucose-PEG conjugate prior to detecting. The incubation may be for any period of time so as to allow for the conjugate to bind to the GLUTs on the hyper-proliferative cell, for example for 5 minutes or longer, for 15 minutes or longer, for 30 minutes or longer or for 1 hour or longer.

Following contacting and optional incubation, the method comprises detecting the detectable label. The method of detecting will depend on the detectable label used. Standard detection methods may be used to detect the detectable label, including the above-mentioned fluorescence microscopy techniques, MRI techniques, PET imaging techniques, and SPECT imaging techniques. Such methods are known to a skilled person and may be performed in accordance with standard, known methods.

The imaging method may be used in vitro to identify a hyper-proliferative cell within a population of cells, or to identify conditions that induce hyper-proliferation within a population of cells. The imaging method is also useful for in vivo imaging, and may be used to identify a hyper-proliferative cell within a subject, including within a solid tumor, or may be used to monitor treatment progression within a subject.

Also contemplated are uses based on the above methods, such as use of a glucose-PEG conjugate as described herein for imaging a hyper-proliferative cell, or use of a glucose-PEG conjugate as described herein in the manufacture of a composition for imaging a hyper-proliferative cell.

The present methods and uses are further exemplified by way of the following non-limited examples.

EXAMPLES

Example 1

The following example demonstrates that glucose modified with poly(ethylene glycol) (PEG) reduces cell proliferation and induces apoptosis in human breast cancer cell line, MCF-7.

Methods

Synthesis of Glucose-PEG-BODIPY (GPB):

Glucose was modified with PEG-conjugated to BODIPY. BODIPY was used as a red fluorescent indicator for cell imaging. A flame dried reaction vial (2 mL) was charged with a solution of glucose-PEG-NH$_2$ (32 mg, 0.1 mmol) and BODIPY 650/665-X (64 mg, 0.1 mmol) under argon, and the mixture was cooled in an ice bath at 0° C. Dry dimethylformamide (DMF; Aldrich, 1 mL) was added dropwise and was stirred at 0° C. for 2 h under argon. The reaction mixture was then brought to room temperature, and continuously stirred for 24 h under argon in the dark. The reaction was monitored by reverse-phase high-pressure liquid chromatography (HPLC; Waters Corporation, USA). After completion of the reaction, DMF was removed under reduced pressure and the blue residue was purified by reverse-phase flash column chromatography using a Combiflash separating system (ISCO Combiflash Companion, USA). The desired fractions were collected and lyophilized to obtain the FR-BODIPY-glucose as a bluish green solid (75 mg, 90%). The final compound was soluble in deionized (DI) water and in a mixture of ethanol and water (volume ratio=1:1). Mass spectral analysis showed a molecular ion peak of 841 (M+1). The structure of glucose-PEG-BODIPY is shown in FIG. 1 and the synthesis scheme, including the preparation of glucose-PEG-NH$_2$, is depicted in FIG. 4.

Synthesis of Glucose-PEG-OH:

A dry reaction vial (10 mL) was charged with glucose-PEG-NH$_2$ (31 mg, 0.1 mmol) and dry DMF (2 mL), and was stirred under argon until complete dissolution was observed. The solution was then cooled to 0° C. in an ice bath. A solution of caprolactone (12 mg, 0.11 mmol) in DMF (1 mL) was added dropwise, and the reaction mixture was stirred overnight and brought to room temperature under argon. After completion of the reaction, as monitored by HPLC and liquid chromatography-mass spectrometry (LC-MS), the solvent was evaporated and purified by precipitation from methanol-diethylether mixture to give the glucose-PEG-OH as a light yellow solid (40 mg, 95%). Mass spectral analysis showed a molecular ion peak of 427 (M+1). The structure of glucose-PEG-OH is shown in FIG. 2.

Conjugation of Glucose to Branched PEG:

A flame dried reaction flask (25 mL) was charged with branched PEG-NH$_2$ (PEG-tetrapropylamine, molecular weight=20 kDa, 500 mg, 0.025 mmol) and glucose (5 mg, 0.0275 mmol) in dry methanol (10 mL), and the mixture was heated at 60° C. under argon for 24 h. The reaction mixture was cooled to 0° C., and reduced with sodium borohydride. The conjugated glucose-branched PEG was purified by precipitation method. The free amino groups in the branched PEG were protected by reaction with caprolactone. The final conjugated product was purified by exhaustive filtration through an Amicon membrane filter (polyethersulfone (PES) membrane, 10 kDa molecular weight cutoff), and lyophilized to obtain a product as a colorless sticky solid. A representative structure of glucose-branched PEG is shown in FIG. 3.

Cell Culture:

Different cancer cell lines, MCF-7 (breast cancer), H1299 (lung cancer), HepG2 (liver cancer), DU145 (prostate cancer), Caco2 (colon cancer) and AGS (gastric cancer) were obtained from American Type Culture Collection (ATCC). Normal breast epithelial cell line (MCF-10A) was used for comparison. The cells were maintained in the growth medium as described by ATCC. Approximately 10,000 cells were seeded onto a 96-well plate. Modified glucose compounds were added to the cells after 24 h of seeding. The cells were further cultured in the presence of the modified glucose compounds for up to 7 days. The medium was changed everyday along with the specified concentration of modified glucose. At the end of the treatment, the cells were assayed for viability using 3-(4,5-dimethylthiazol-2-yl)-2,5-diphenyl tetrazolium bromide (MTT) assay.

MTT Assay:

MTT assay was performed using the TACS™ MTT cell proliferation assay kit (Trevigen Inc, Md., USA). Briefly, after treatment of cells, 10 µl of MTT reagent was added and incubated at 37° C. for 4 h. The cells were lysed using detergent for 4 h at room temperature. The absorbance was measured in a standard plate reader at 570 nm.

Competition Assay:

Competition assay was performed to demonstrate the specificity of the GPB binding to the GLUTs. GPB binding to the cell surface could be quantified by measuring the fluorescence intensity. Addition of unlabeled glucose at different concentrations (10 mM, 20 mM, 30 mM, 35 mM and 40 mM) to the media competed with the GPB binding, leading to the differences in the fluorescence intensity. Cells were incubated with GPB and various concentrations of glucose for 30 min at 37° C. The medium was removed and the cells were washed briefly with PBS twice. The fluorescence intensity was measured with an excitation of 488 nm and an emission of 522 nm. The fluorescence intensity was normalized by that of the control cells.

Imaging:

The MCF-7 cells were seeded on a 6-well plate at least 24 h prior to imaging. The cells were incubated with GPB (200 µM) for 1 h. The cells were washed with PBS (without calcium and magnesium) thrice. Live imaging was performed with fluorescence microscopy. Metamorph (Molecular Devices, USA) and Image J (freeware from NIH, USA) were used for image capturing and processing.

Results

Figure 5:
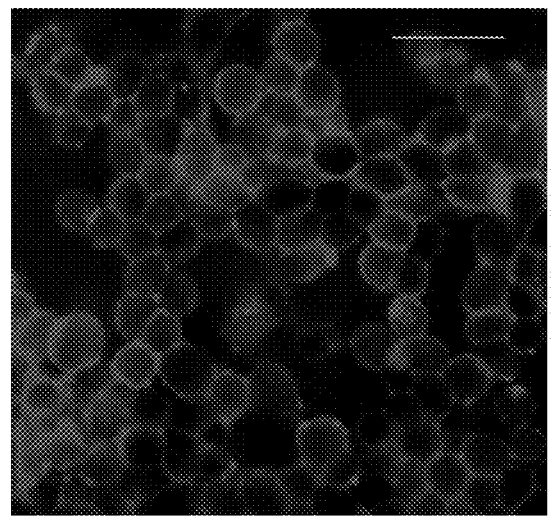
FIG. 5: Fluorescence image of MCF-7 cells labeled with GPB. MCF-7 cells grown overnight were incubated with 500 µM of GPB in the growth medium for 30 min. They were washed with PBS before fluorescence imaging. Scale bar=500 µm.
Figure 6:
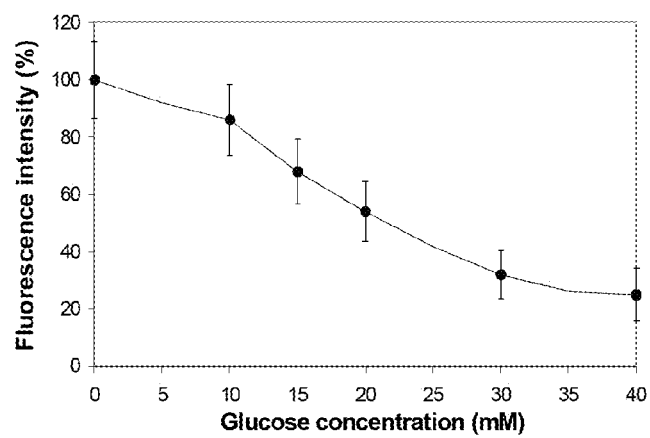
FIG. 6: Competition assay. Competition binding assay was performed in the presence of different concentrations of glucose added to the medium containing GPB (200 µM). The cells were incubated for 30 min at 37° C. The cells were washed with PBS, and the total intensity was measured using a plate reader. The total intensity for the control cells with GPB and without glucose was taken as 100%.

To test the hypothesis that modified glucose could be utilized for cancer therapy, a fluorescent tag (BODIPY) was conjugated onto glucose via PEG. This GPB was used in the initial imaging studies. Fluorescence imaging of MCF-7 cells fed with GPB clearly indicated that the GPB molecules were localized on the plasma membrane of the cells (FIG. 5). The binding of the modified GPB was challenged with different concentrations of glucose. The competition binding assay suggested that glucose competed with the GPB in binding to the GLUTs (FIG. 6).

Figure 7:
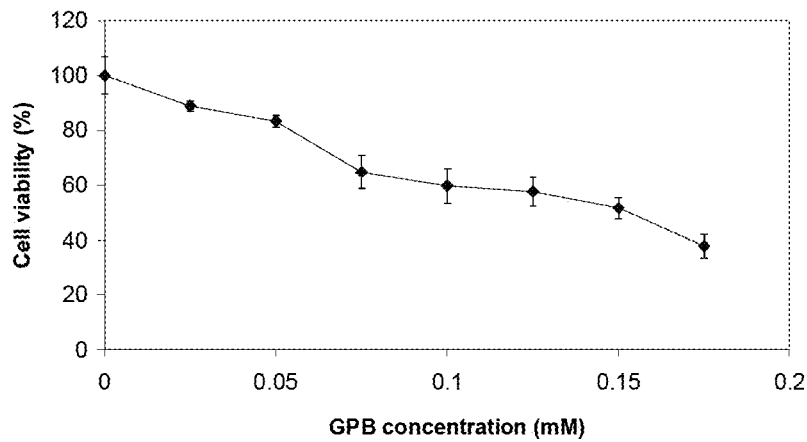
FIG. 7: Dose-dependent cell death in MCF-7 cells. MCF-7 cells were seeded onto 96-well plates at least 24 h prior to the experiment. Different concentrations of GPB were added and further cultured for 7 days. The medium was changed every day along with the specified GPB concentration. MTT assay was performed to assess the cell viability. Control cells received no GPB treatment. Cell viability was normalized with that of the control cells.
Figure 8:
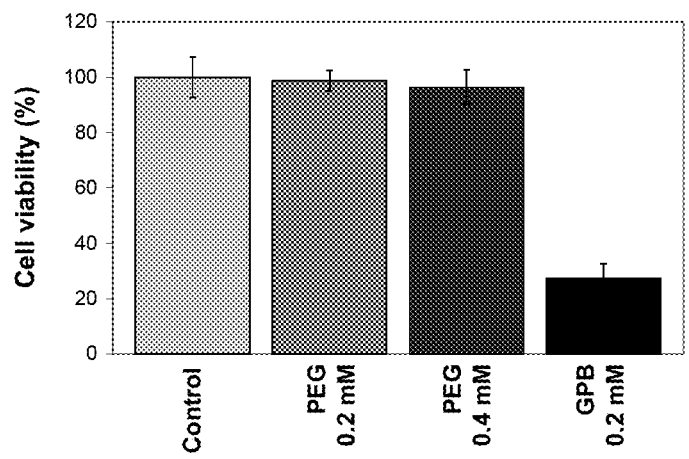
FIG. 8: Effect of PEG on MCF-7 cells. The MCF-7 cells were treated with 200 µM and 400 µM of PEG, and 200 µM of GPB. The cells were treated as described in FIG. 3, followed by the MTT assay.

Dose-dependent effect of GPB on the MCF-7 cells was examined. The cell viability assay (MTT assay) was performed on cells treated with different GPB concentrations. There was a gradual dose-dependent decrease in the cell viability with increasing GPB concentration (FIG. 7). ~63% reduction in cell viability was observed when the cells were treated with 200 µM of GPB (FIG. 8). PEG alone at concentrations of 200 µM and 400 µM did not have any effect on the MCF-7 cells (FIG. 8). However, cells treated with 200 µM of GPB showed a drastic reduction in cell viability (~70%) (FIG. 8).

Figure 9:
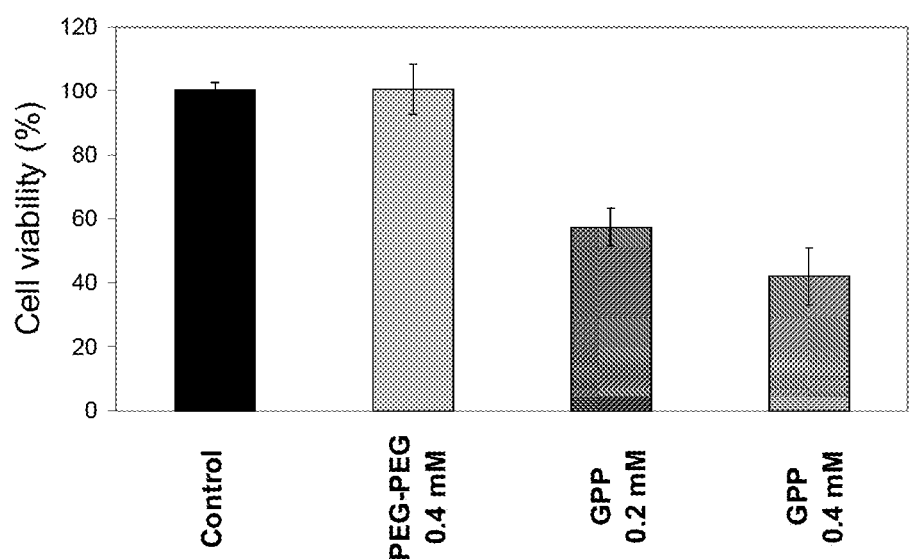
FIG. 9: Effect of GPP on MCF-7 cells. The MCF-7 cells were cultured on a 96-well plate. 200 µM and 400 µM of GPP were added to the cells, and the cell viability was analyzed after 7 days of culture. The medium was changed every day with the specified GPP concentration. Value for the control cells without GPP was taken as 100% viable.

A new compound was also synthesized to replace the BODIPY in GPB with another PEG molecule. This new compound has two PEGs conjugated to the glucose (glucose-PEG-PEG or GPP). The cell viability was reduced to 57% and 42% at 200 µM and 400 µM of GPP, respectively (FIG. 9). In contrast, the cell viability was not affected by 400 µM of PEG-PEG.

A further strategy to increase the levels of cell death was to further modify the glucose with a branched structure. Glucose was coupled to a branched PEG (4-arm PEG or BrP) as described in the methods. The resulting compound was designated as glucose-conjugated branched PEG or GBrP. 200 µM of GBrP could reduce the viability of MCF-7 breast cancer cells by >90%, where as 200 µM of branched PEG only decreased the viability of the same cell line by 7% (see Table 1). Thus, GBrP was even more effective at inhibiting cell viability than GPB and GPP. In contrast, Table 1 also shows that 200 µM of GBrP reduced the viability of normal breast cells by only 29%. This illustrates the ability of GBrP to preferentially target cancer cells. GBrP was also demonstrated to significantly inhibit the viability of various different cancer cell lines (see Table 1).

Figure 10:
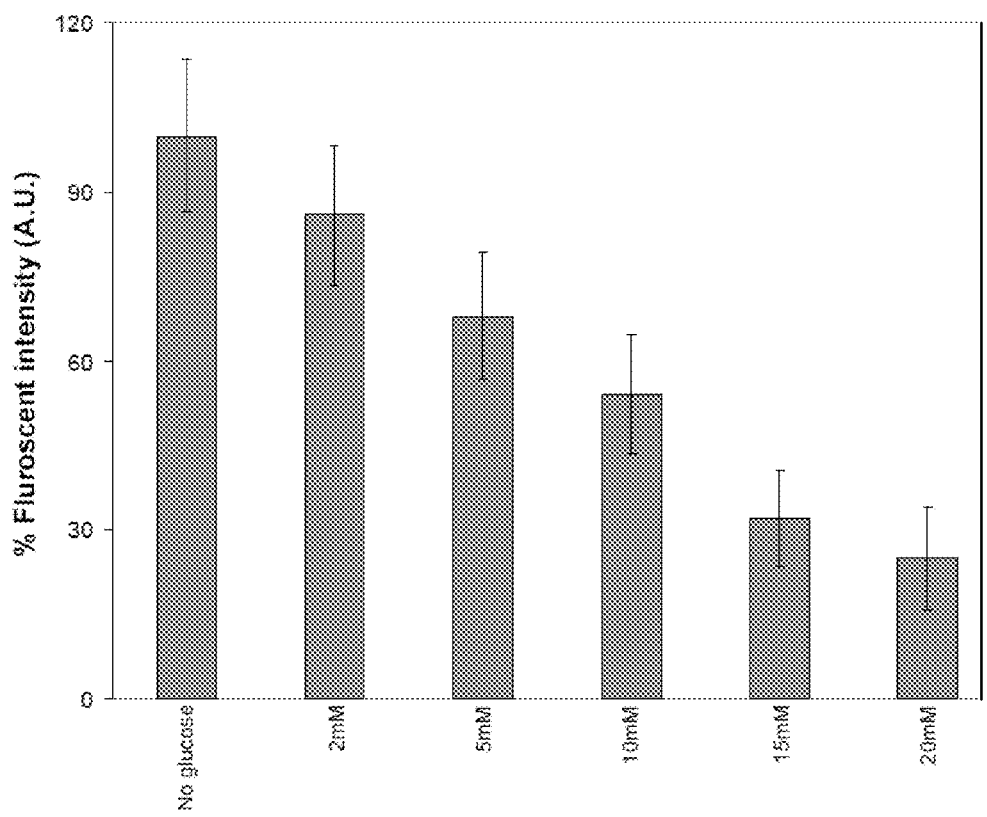
FIG. 10: Binding of GBP to GLUT1. Human breast cancer cells (MCF-7) were incubated with 200 µM of GPB in the presence of the increasing concentrations of un-modified glucose. After 30 minutes the fluorescence intensity was measured using a plate reader.

A glucose competition assay was carried out to confirm that the modified glucose-PEG is binding to the GLUT1 receptors. Increasing concentrations of un-modified glucose were used. The human breast cancer cells (MCF-7) were incubated with 200 µM of GPB in the presence of the increasing concentrations of un-modified glucose. After 30 minutes the fluorescence intensity was measured using a plate reader. As indicated in FIG. 10, the intensity of the fluorescence decreases with the increase in un-modified glucose, indicating that the un-modified glucose is competing for the GLUT1 receptor.

Figure 11:
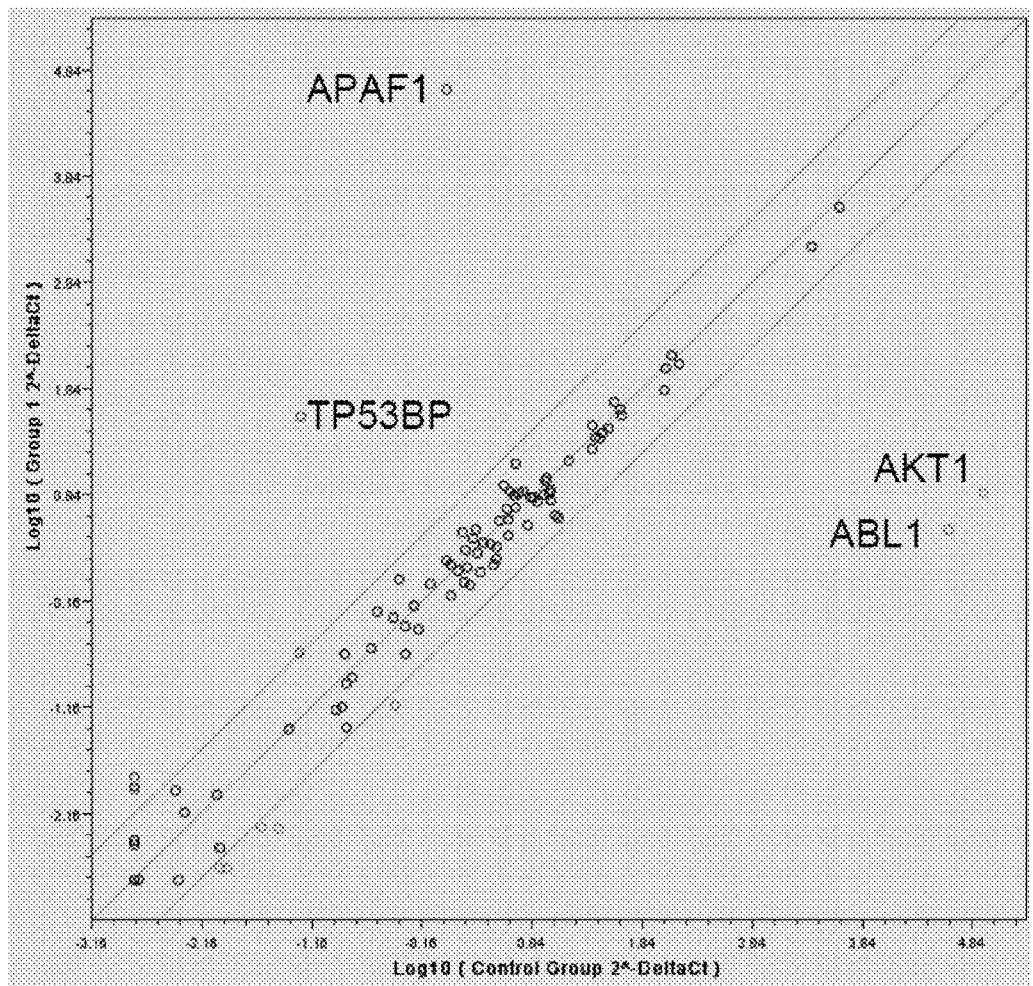
FIG. 11: Gene expression in lung cancer cells treated with GBrP. Human lung cancer cells (H1299) were treated for 3 days with 200 µM of modified glucose (GBrP). Control cells were prepared without treatment. Total RNA was extracted from the cells and reverse transcribed. A PCR array containing primers to identify the apoptotic pathway was used to identify the apoptosis pathway between control and treated cells in lung cancer cells.
Figure 12:
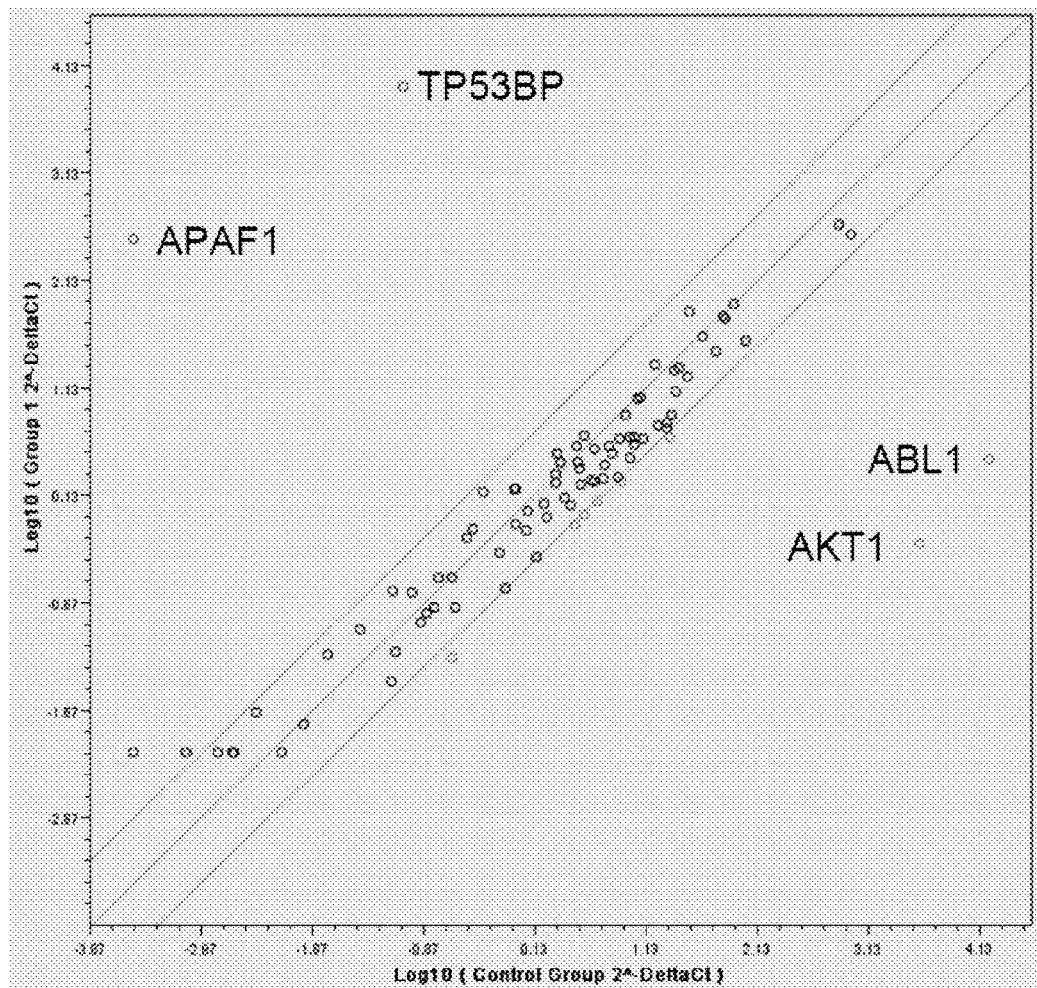
FIG. 12: Gene expression in prostate cancer cells treated with GBrP. Human prostate cancer cells (DU145) were treated for 3 days with 200 µM of modified glucose (GBrP). Control cells were prepared without treatment. Total RNA was extracted from the cells and reverse transcribed. A PCR array containing primers to identify the apoptotic pathway was used to identify the apoptosis pathway between control and treated cells in prostate cancer cells.

Gene expression analysis was carried out to understand the apoptosis pathway during the modified glucose mediated cell death. Human lung cancer cells (H1299) (FIG. 11) or human prostate cancer cells (DU145) (FIG. 12) were treated for 3 days with 200 µM of modified glucose (GBrP). Control cells were prepared without treatment. Total RNA was extracted from the cells and reverse transcribed. A PCR array containing primers to identify the apoptotic pathway was used to identify the apoptosis pathway between control and treated cells in lung or prostate cancer cells. The amplification data is represented in a scatter plot with allowable variations. As seen in FIGS. 11 and 12, AKT1 and ABL1 were down regulated while APAF1 and TP53BP were upregulated.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. Unless defined otherwise all technical and scientific terms used herein have the same meaning as commonly understood to one of ordinary skill in the art to which this invention belongs.

All lists or ranges provided herein are intended to include any sub-list or narrower range falling within the recited list or range.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

1. Flier J S, Mueckler M M, Usher P, Lodish H F (1987). Elevated levels of glucose transport and transporter messenger RNA are induced by ras or src oncogenes. Science 235:1492-1495.
2. Younes M, Brown R W, Mody D R, Fernandez L, Laucirica R (1995). GLUT1 expression in human breast carcinoma: Correlation with known prognostic markers. Anticancer Res 15:2895-2898.
3. Haber R S, Weiser K R, Pritsker A, Reder I, Burstein D E (1997). GLUT1 glucose transporter expression in benign and malignant thyroid nodules. Thyroid 7:363-367.
4. Yamamoto T, Seino Y, Fukumoto H, Koh G, Yano H, Inagaki N, Yamada Y, Inoue K, Manabe T, Imura H (1990). Over-expression of facilitative glucose transporter genes in human cancer. Biochem Biophys Res Commun 170:223-230.
5. Kurata T, Oguri T, Isobe T, Ishioka S, Yamakido M (1999). Differential expression of facilitative glucose transporter (GLUT) genes in primary lung cancers and their liver metastases. Jpn J Cancer Res 90:1238-1243.
6. Nishioka T, Oda Y, Seino Y, Yamamoto T, Inagaki N, Yano H, Imura H, Shigemoto R, Kikuchi H (1992). Distribution of the glucose transporters in human brain tumors. Cancer Res 52:3972-3979.
7. Brown R S and Wahl, R L (1993). Overexpression of Glut-1 glucose transporter in human breast cancer. An immunohistochemical study. Cancer 72: 2979-2985.
8. Nagase Y, Takata K, Moriyama N, Aso Y, Murakami T, Hirano H (1995). Immunohistochemical localization of glucose transporters in human renal cell carcinoma. J Urol 153:798-801.
9. Baer S C, Casaubon L, Younes M (1997). Expression of the human erythrocyte glucose transporter Glut1 in cutaneous neoplasia. J Am Acad Dermatol 37:575-577.
10. Ogawa J, Inoue H, Koide S (1997). Glucose-transporter-type-I-gene amplification correlates with sialyl-Lewis-X synthesis and proliferation in lung cancer. Int J Cancer 74:189-192.
11. Haber R S, Rathan A, Weiser K R, Pritsker A, Itzkowitz S H, Bodian C, Slater G, Weiss A, Burstein D E (1998). GLUT1 glucose transporter expression in colorectal carcinoma: A marker for poor prognosis. Cancer 83:34-40.
12. Wang B Y, Kalir T, Sabo E, Sherman D E, Cohen C, Burstein D E (2000). Immunohistochemical staining of GLUT1 in benign, hyperplastic, and malignant endometrial epithelia. Cancer 88:2774-2781.
13. Cantuaria G, Fagotti A, Ferrandina G, Magalhaes A, Nadji M, Angioli R, Penalver M, Mancuso S, Scambia G (2001). GLUT-1 expression in ovarian carcinoma: Association with survival and response to chemotherapy. Cancer 92:1144-1150.
14. Rudlowski C, Becker A J, Schroder W, Rath W, Buttner R, Moser M (2003). GLUT1 messenger RNA and protein induction relates to the malignant transformation of cervical cancer. Am J Clin Pathol 120:691-698.
15. Younes M, Brown R W, Mody D R, Fernandez L, Laucirica R (1995). GLUT1 expression in human breast carcinoma: Correlation with known prognostic markers. Anticancer Res 15:2895-2898.
16. Ravazoula P, Batistatou A, Aletra C, Ladopoulos J, Kourounis G, Tzigounis B (2003). Immunohistochemical expression of glucose transporter Glut1 and cyclin D1 in breast carcinomas with negative lymph nodes. Eur J Gynaecol Oncol 24:544-546.
17. Beckner M E, et al. (1990). Glycolysis as primary energy source in tumor cell chemotaxis. J. Natl Cancer Inst 82:1836-1840.
18. Newsholme E A, Board M (1991). Application of metabolic-control logic to fuel utilization and its significance in tumor cells. Adv Enzyme Regul 31:225-246.
19. Warburg O (1956). On the origin of cancer cells. Science 123:309-314.
20. Shim H, Dolde C, Lewis B C, Wu C S, Dang G, Jungmann R A, Dalla-Favera R, Dang C V (1997). c-Myc transactivation of LDH-A: Implications for tumor metabolism and growth. Proc Natl Acad Sci USA 94:6658-6663.
21. Board M, Humm S, Newsholme E A (1990). Maximum activities of key enzymes of glycolysis, glutaminolysis, pentose phosphate pathway and tricarboxylic acid cycle in normal, neoplastic and suppressed cells. Biochem J 265:503-509.
22. Mazurek S, Grimm H, Boschek C B, Vaupel P, Eigenbrodt E (2002). Pyruvate kinase type M2: A crossroad in the tumor metabolome. Br J Nutr 87:S23-S29.
23. Hennipman A, van Oirschot B A, Smits J, Rijksen G, Staal G E (1988). Glycolytic enzyme activities in breast cancer metastases. Tumor Biol 9:241-248.
24. Zamora-Leon S P, Golde D W, Concha II, Rivas C I, Delgado-Lopez F, Baselga J, Nualart F, Vera J C (1996). Expression of the fructose transporter GLUT5 in human breast cancer. Proc Natl Acad Sci USA 93:1847-1852.
25. Connors T A, Cox P J, Farmer P B, Foster A B, Jarman M (1974). Some studies of the active intermediates formed in the microsomal metabolism of cyclophosphamide and iphosphamide. Biochem Pharmacol 23:115-129.
26. Reske S N, Grillenberger K G, Glatting G, Port M, Hildebrandt M, Gansauge F, Beger H G (1997). Overexpression of glucose transporter 1 and increased FDG uptake in pancreatic carcinoma. J Nucl Med 38:1344-1348.
27. Veyhl M, Wagner K, Volk C, Gorboulev M, Baumgarten K, Weber W-M, Schaper M, Bertram B, Wiessler M, Koepsell H (1998). Transport of the new chemotherapeutic agent b-D-glucosylisophosphoramide mustard (D-19575) into tumor cells is mediated by the Na$^+$-D-glucose cotransporter SAAT1. Proc Natl Acad Sci USA 95:2914-2919.
28. Pohl J, Bertram B, Hilgard P, Nowrousian M R, Stuben J, Wiebler M (1995). D-19575—A sugar-linked isophosphoramide mustard derivative exploiting transmembrane glucose transport. Cancer Chemother Pharmacol 35:364-370.

29. Ball H, Wick A, Sanders C (1957). Influence of glucose anti-metabolites on the Walker tumor. Cancer Res 17:235-239.

30. Laszlo J, Humphreys S, Goldin A (1960). Effects of glucose analogues (2-deoxy-D-glucose, 2-deoxy-D-galactose) on experimental tumors. J Natl Cancer Inst 24:267-280.

31. Kern K, Norton J (1987). Inhibition of established rat fibrosarcoma growth by the glucose antagonist 2-deoxy-D-glucose. Surgery 102:380-385.

32. Nelson C, Wang J, Leav I, Crane P (1996). The interaction among glucose transport, hexokinase, and glucose-6-phosphatase with respect to 3H-2-deoxyglucose in murine tumor models. Nuclear Med Biol 23:533-541.

33. Aft R L, Zhang F W, Gius D (2002). Evaluation of 2-deoxy-D-glucose as a chemotherapeutic agent: Mechanism of cell death. Br J Cancer 87:805-812.

34. Ko Y, Pedersen P, Geschwind J (2001). Glucose catabolism in the rabbit VX2 tumor model for liver cancer: Characterization and targeting hexokinase. Cancer Lett 173:83-91.

35. Noguchi Y, Saito A, Miyagi Y, Yamanaka S, Marat D, Doi C, Yoshikawa T, Tsuburaya A, Ito T, Satoh S (2000). Suppression of facilitative glucose transporter 1 mRNA can suppress tumor growth. Cancer Lett 1544:175-182.

36. Rastogi S, Banerjee S, Chellappan S, Simon G R (2007). Glut-1 antibodies induce growth arrest and apoptosis in human cancer cell lines. Cancer Lett 257:244-251.

37. Lee G Y, Kim S K, Byun Y (2007). Glucosylated heparin derivatives as non-toxic anti-cancer drugs. J Control Release 123:46-55.

38. Airley R E, Mobasheri A (2007). Hypoxic regulation of glucose transport, anaerobic metabolism and angiogenesis in cancer: Novel pathways and targets for anticancer therapeutics. Chemotherapy 53:233-256.

39. Maher J C, Wangpaichitr M, Savaraj N, Kurtoglu M, Lampidis T J (2007). Hypoxia-inducible factor-1 confers resistance to the glycolytic inhibitor 2-deoxy-D-glucose. Mol Cancer Ther 6:732-741.

40. Cao X, Fang L, Gibbs S, Huang Y, Dai Z, Wen P, Zheng X, Sadee W, Sun D (2007). Glucose uptake inhibitor sensitizes cancer cells to daunorubicin and overcomes drug resistance in hypoxia. Cancer Chemother Pharmacol 59:495-505.

41. Grover-McKay M, Walsh S A, Seftor E A, Thomas P A, Hendrix M J (1998). Role for glucose transporter 1 protein in human breast cancer. Pathol Oncol Res 4:115-120.

42. Kawamura T, Kusakabe T, Sugino T, Watanabe K, Fukuda T, Nashimoto A, Honma K, Suzuki T (2001). Expression of glucose transporter-1 in human gastric carcinoma: Association with tumor aggressiveness, metastasis, and patient survival. Cancer 92:634-641.

43. Rivenzon-Segal D, Rushkin E, Polak-Charcon S, Degani H (2000). Glucose transporters and transport kinetics in retinoic acid-differentiated T47D human breast cancer cells. Am J Physiol Endocrinol Metab 279:E508-E519.

What is claimed is:

1. A glucose-PEG conjugate comprising a moiety selected from the group consisting of:

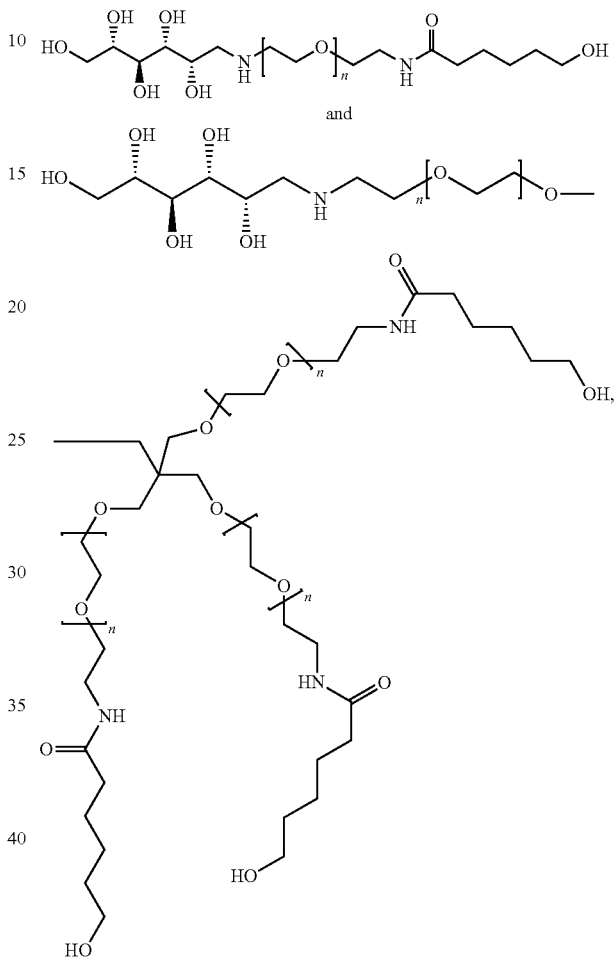

wherein each n is independently from 2 to 500.

2. The glucose-PEG conjugate of claim 1 further comprising a detectable label attached to the glucose-PEG conjugate, wherein the detectable label is a PET label, an SPECT label, an MRI label, a quantum dot label, a coloured label, a fluorescent label, or a radiolabel.

3. The glucose-PEG conjugate of claim 2 comprising

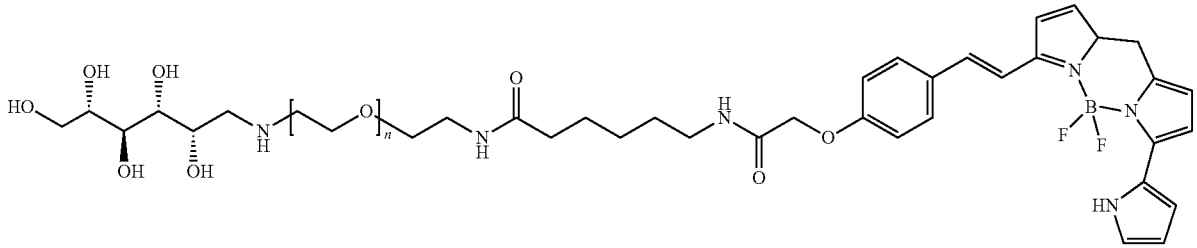

4. A method of imaging a hyper-proliferative cell comprising contacting a hyper-proliferative cell with a glucose-PEG conjugate of claim 2; and detecting the detectable label.

5. The method of claim 4 wherein detecting involves fluorescence microscopy, positron emission tomography imaging, single photon emission computed tomography imaging or magnetic resonance imaging.

6. The method of claim 4 wherein the cell is associated with a proliferative disorder.

7. The method of claim 6 wherein contacting comprises administering an effective amount of the glucose-PEG conjugate at the site of a hyper-proliferating cell in a subject.

8. The method of claim 4 further comprising contacting the cell with a chemotherapeutic agent.

9. The method of claim 6 further comprising contacting the cell with a chemotherapeutic agent.

10. A pharmaceutical composition comprising a glucose-PEG conjugate of claim 1.

\* \* \* \* \*